United States Patent [19]

Fedorov et al.

[11] Patent Number: 4,605,411
[45] Date of Patent: Aug. 12, 1986

[54] ANTERIOR-CHAMBER INTRAOCULAR PROSTHETIC LENS

[75] Inventors: Svyatoslav N. Fedorov; Sergei I. Anisimov; Alexandr A. Karavaev; Vladimir G. Kisellev, all of Moscow; July A. Juzhelevsky, Leningrad; Evgeny I. Degtev, Moscow, all of U.S.S.R.

[73] Assignee: Moskovsky Nauchno-Issledovatelsky Institut Mikrokhirurgii Glaza, Moscow, U.S.S.R.

[21] Appl. No.: 777,022

[22] Filed: Sep. 17, 1985

[30] Foreign Application Priority Data

Sep. 27, 1984 [SU] U.S.S.R. .............................. 3795791

[51] Int. Cl.⁴ .............................................. A61F 2/16
[52] U.S. Cl. ............................................................ 623/6
[58] Field of Search ................................................ 623/6

[56] References Cited

U.S. PATENT DOCUMENTS

| 4,253,200 | 3/1981 | Kelman | 623/6 |
| 4,254,510 | 3/1981 | Tennant | 623/6 |
| 4,277,851 | 7/1981 | Choyce | 623/6 |
| 4,442,553 | 4/1984 | Hessburg | 623/6 |
| 4,535,488 | 8/1985 | Haddad | 623/6 |

FOREIGN PATENT DOCUMENTS 545352  5/1977  U.S.S.R. .............................. 623/6

OTHER PUBLICATIONS

"Nuevos Modelos de Lentes Plasticas de Camara Anterior" by Barraquer, Joaquin, *Anales del Instituto Barraquer*, Sep. 1961, pp. 345-352, vol. II, No. 3.

*Primary Examiner*—Ronald L. Frinks
*Attorney, Agent, or Firm*—Burgess, Ryan & Wayne

[57] ABSTRACT

An optical lens is secured to supporting setting platforms, of which one is formed by a circumferential sector conjugated with the optical element (lens) so as to form shoulders. The other of said platforms is formed by two rounded-off radial portions conjugated with each other and with the optical element. Both of the platforms have biconcave surfaces, and one of these is thicker than the other.

2 Claims, 9 Drawing Figures

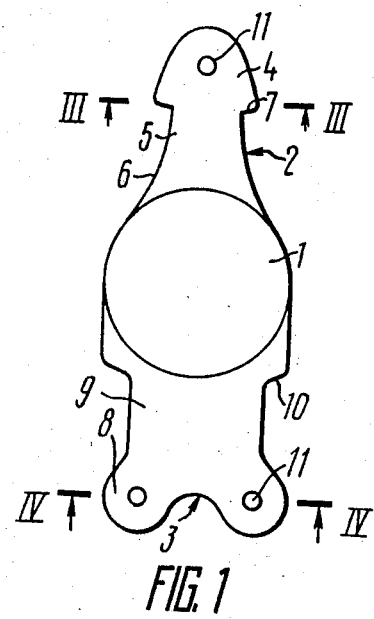
FIG. 1
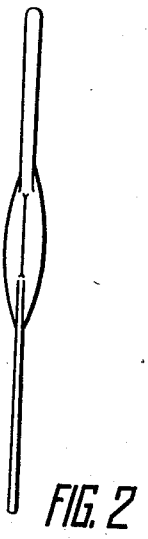
FIG. 3
FIG. 4
FIG. 2
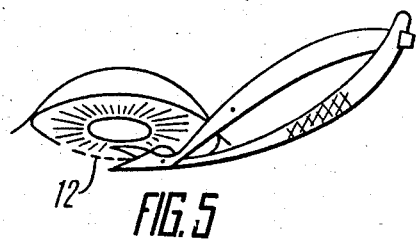
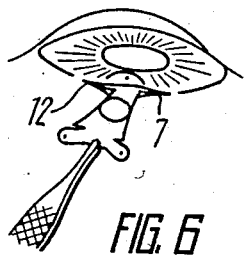
FIG. 5
FIG. 6
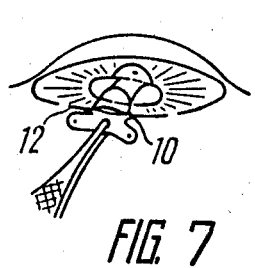
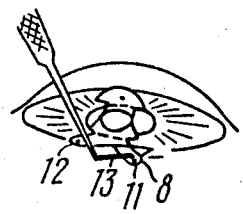
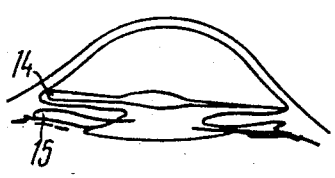
FIG. 7
FIG. 8
FIG. 9

ANTERIOR-CHAMBER INTRAOCULAR PROSTHETIC LENS

FIELD OF THE INVENTION

The present invention relates generally to ophthalmology and more specifically to an anterior-chamber intraocular prosthetic lens or lenticulus inserted into a patient's eye after, e.g., surgery for cataract extraction.

BACKGROUND OF THE INVENTION

There are hitherto known a rather great number of diverse types of intraocular prosthetic lenses otherwise named lenticuli, comprising an optical element (usually a lens), and supporting setting elements adapted for the prosthetic lens to insert into a patient's eye. The supportng elements were usually made from thin wire structures curved in an arcuate form or as loops, or else as platforms. One of such prosthetic lenses with the supporting elements as platforms is described in U.S. Pat. No. 4,277,851 issued on July 14, 1981.

Such a prosthetic lens comprises an optical element made fast in between two diametrically opposite supporting elements, each of these being in fact an arcuate supporting platform intended for being fixed in the anterior eye chamber. Each of the supports has coplanar legs running in the opposite directions as far as the boundary of the eye chamber. Recesses are provided in the outside lateral edges of the supporting elements, said recesses being located on any side of a transverse line passing square with said lateral edges and through the centre of the prosthetic lens. The posterior surface of the optical element is situated underneath of the plane of the legs.

However, the aforediscussed intraocular lens implant suffers from a number of cardinal disadvantages, since unilateral implantation of such a prosthetic lens, wherein the posterior surface of the optical element is arranged above the plane of the legs results in a high degree of anisoiconia. Implantation of the intraocular prosthetic lens of such a construction causes emptying of the anterior eye chamber, which in turn results in injury to the endothelial cells of the cornea. Moreover, even an inconsiderable discrepancy between the lens size and the diameter of the anterior eye chamber, when the length of the prosthetic lens is less than the aforesaid dimension of the patient's eye, mobility of the prosthetic lens may result, which might lead to some postoperative complications, such as corneal edema or iritides.

SUMMARY OF THE INVENTION

It is an object of the present invention to provide an anterior-chamber intraocular prosthetic lens which would make it possible to avoid emptying of the anterior eye chamber at the instant of its implantation.

It is another object of the present invention to provide an anterior-chamber intraocular prosthetic lens which would make it possible to reduce the contact area of the supporting elements with the reactive tissue of the iris.

It is one more object of the present invention to provide an intraocular prosthetic lens which would be capable of better delivery of the aqueous humor to the angle of the anterior eye chamber.

There is worth noting, among objects of the invention, one of better centring of an intraocular prosthetic lens, as well as improved conditions of the operative procedure involved.

Said and other objects of the invention are attained due to the fact that in an intraocular prosthetic lens, comprising an optical element secured between two diametrically opposite supporting setting elements, according to the invention, one of said platforms is formed by a circumferential sector, while the other platform is formed by two rounded-off symmetrically arranged portions. The circumferential sector and the rounded-off portions are conjugated with the optical element through transitional portions having shoulders. Both of the platforms have a biconcave cross-sectional shape and are substantially coplanar, one of these being thicker than the other.

The herein-proposed construction of an intraocular prosthetic lens possesses quite a number of substantial advantages which are briefly considered hereinbelow.

Provision of the lateral concave sides of the transitional portions and shoulders in the zone of joining with the sector makes it possible to avoid emptying of the anterior eye chamber at the instant of implanting an intraocular prosthetic lens, while the circumferential sector is practically unobstructedly passed through the operative discision. Provision of the shoulders on the other conjugated portion enables one to avoid emptying of the anterior eye chamber at the instant of passing the platform with rounded-off portions. This in turn makes it possible to fill up the anterior eye chamber at a minimum consumption of the irrigation liquid which is sufficient to maintain such a depth of the anterior eye chamber that is necessary to rule out the contact of the intraocular prosthetic lens with the endothelium at the moment of implanting the former into the patient's eye.

Thus, provision of projections on the supporting platforms makes it possible, at the instant of implanting an intraocular prosthetic lens, to fill up the anterior eye chamber with the irrigation liquid but twice rather than to carry out permanent irrigation, thereby minimizing the irrigation liquid consumption. The biconcave surfaces of the platforms of the supporting setting elements make it possible to reduce their contact area with the reactive tissue of the iris. Besides, the supporting elements having concave surfaces and adjacent to the iris, define a "tunnel" along with the outer iridic surface, with the result that delivery of the aqueous humor and the substrates contained therein to the angle of the anterior eye chamber is improved in the zone of an intimate contact with the supporting setting elements. This also contributes to better trophicity in the aforesaid zone and renders such a complication as secondary glaucoma less probable. Dissimilar thickness of the supporting elements enables one to attain correct centring of the prosthetic lens mass and thereby to avoid development of twisting moment or torque. Furthermore, in cases of a slight dimensional discrepancy, when the length of an intraocular prosthetic lens is less than the diameter of the anterior eye chamber, it is due to different thickness of the supporting elements that the thicker element wedges in the zone of the angle of the anterior eye chamber that does not protrude beyond the boundary of the scleral spur, thus preventing the intraocular prosthetic lens from rotation and displacement.

BRIEF DESCRIPTION OF THE DRAWINGS

In what follows the present invention is illustrated by a detailed description of a specific but not limiting embodiment of an intraocular prosthetic lens, according to the invention to be read in conjunction with the accompanying drawings, wherein:

FIG. 1 is a plan view of an intraocular prosthetic lens, according to the invention;

FIG. 2 is a side view of FIG. 1;

FIG. 3 is a section taken on the line III—III in FIG. 1;

FIG. 4 is a view taken along the line IV—IV in FIG. 1; and

FIGS. 5 through 9 represent shcematically an eye when an intraocular prosthetic lens is being implanted therein, according to the invention.

DESCRIPTION OF THE PREFERRED EMBODIMENTS

Now let us refer to FIG. 1 which makes it evident that the intraocular prosthetic lens, according to the invention, comprises an optical element 1 and two diametrically opposite supporting setting elements shaped as platforms 2 and 3. One of the supporting elements is in fact a platform incorporating a circumferential sector 4 situated at the platform end most removed from the optical element 1. The sector 4 is joined with the optical element 1 through a conjugate portion 5 having concave lateral sides 6 that form shoulders 7 in the zone of junction with the sector 4.

Another platform 3 servicing as the other supporting element, is formed by two rounded-off portions 8 arranged symmetrically with respect to a plane passing through the centre of the optical element and in the middle of the sector 4. Generally speaking, it may be assumed that the rounded-off portions 8 are arranged radially. The rounded-off portions 8 are conjugated with each other and joined with the optical element 1 through a transitional portion 9, thus forming projections 10 that face a direction opposite to the optical element 1. As it can well be seen from FIGS. 3 and 4, both of said platforms have biconcave surfaces and, as shown in FIG. 2, they are arranged in a common plane which coincides with the optical element central plane. It can also be seen from comparison of FIGS. 3 and 4, and from FIG. 2 that one of the platforms is thicker than the other. Through holes 11 are provided in the platform 2 and in the rounded-off portions 8, aimed at a better supply of the angle of the anterior eye chamber in this zone, thus reducing the incidence of the post-operative complications.

The element described above can be manufactured by moulding from an appropriate elastic material.

The implantation procedure of the herein-proposed intraocular prosthetic lens occurs as follows. A 3-mm long incision of the cornea is performed under local anesthesia at 5 o'clock (FIG. 5), whereupon an irrigation system (omitted in the Drawing) is introduced into the anterior eye chamber. Then a 4–6 mm long incision 12 is made along the dial from 11 and 2 o'clock. The anterior crystalline capsule is slit open according to the routine technique applicable for extracapsular cataract extraction. The nucleus of the lens and the crystalline mass are removed likewise typically of the extracapsular cataract extraction. Thereupon the intraocular prosthetic lens is taken hold of through a forceps by the transitional portion 9 and is then inserted into the anterior eye chamber with the supporting setting element 2 forward (FIG. 6). As a result, the lips of the corneoscleral incision 12 are brought together past the shoulders 7 to fix the supporting setting element 2 in position, whereby the shoulders 7 perform additional tamponing of the incision 12 which makes it possible to fill up the anterior eye chamber at a minimum consumption of the irrigation liquid. This, in turn, renders it possible to minimize the injurious effect of the irrigation liquid itself and to avoid damage to the endothelium of the corneal layer and to the posterior crystalline capsule that may be inflicted by the intraocular prosthetic lens in the course of its further implantation. Once the anterior eye chamber has been filled up with the irrigation liquid, the prosthetic lens makes its further progress to the anterior eye chamber until the horizontal portions of the projections 10 of the supporting element 3 get held by the lips of the incision 12 which are brought together past the bases of the projections 10 (FIG. 7). Thus, the provision of the projections on the supporting elements, and of the shoulders formed by the concave lateral sides of the supporting element 2 makes it possible to perform implantation of an intraocular prosthetic lens strictly on a preselected axis and with minimized mechanical efforts applied. This, in addition, reduces the incidence of the intraoperative complications, such as traumatic lesion of the corneal endothelium, rupture of the posterior crystalline capsule followed by vitreoptosis, irido- and goniodialysis, as well as reduces the operating time due to a decreased number of surgeon's manipulations involved in the prosthetic lens implanting procedure. At the next stage the rounded-off portions of the supporting element 3 protruding beyond the lips of the incision 12, are buried into the bay of the angle of the anterior eye chamber. In this case the rounded-off portions 8 of the supporting element 3 are set behind the scleral lip 13 of the incision 12 with the aid of a spatula passed through the hole 11 in the supporting element 3 (FIG. 8). Next the anterior eye chamber is restored, hermetical sutures are applied to the wound, and a monocular eye bandage is placed.

The supporting element 2 is made thicker than the element 3, whereby a mass-balanced system of supporting elements is created, thus preventing the development of a twisting moment that is liable to occur with movement of an artiphakial eye. In addition, this enables one to compensate for such a dimensional discrepancy that occurs when the length of a prosthetic lens is less than the diameter of the anterior eye chamber, this being due to the fact that the thicker supporting element 2 is stably fixed at the angle 14 of the anterior eye chamber without getting in contact with the latter through its end-face portion 15 (FIG. 9).

Practical application of the present invention makes it possible to avoid damage to the endothelial cells of the cornea, corneal edema within the postoperative period, and to render postoperative glaucoma less probable. Besides, the proposed construction of an intraocular prosthetic lens contributes to better operating conditions and makes it possible to reduce the operating time.

While in the foregoing, a preferred embodiment of an intraocular prosthetic lens has been described, according to the invention, as well its implantation techniques, it will be understood that various changes and modifications may be made in the construction of the intraocular prosthetic lens of the invention within the limits of the spirit and scope of the present invention.

What is claimed is:

1. An intraocular prosthetic lens, comprising an optical element, two diametrically opposite supporting setting elements shaped as platforms,
    one of said platforms formed by a circumferential sector situated on the platform side distant from the optical element, and by a portion of said sector conjugated with the optical element, said conjugate portion having concave lateral sides forming shoulders at the place of joining with the sector, the other of said platforms is formed by two rounded-off portions arranged symmetrically with respect to a plane passing through the centre of the optical element and substantially radially, said roundedoff portions being conjugated with each other and with the optical element through a transitional portion, projections being thus formed that face a direction opposite to the optical element, both of said platforms have a biconcave crosssectional shape and are arranged in a common plane which is coplanar with the central plane of the optical element, and one of said platforms is thicker than the other.

2. An intraocular prosthetic lens as claimed in claim 1, wherein through-holes are provided in the sector-shaped platform and in the rounded-off portions.

* * * * *